US008652182B1

(12) United States Patent
Walker et al.

(10) Patent No.: US 8,652,182 B1
(45) Date of Patent: Feb. 18, 2014

(54) BONE PLATE WITH RETAINER AND STOP FOR SCREW LOCK

(75) Inventors: Lawrence Walker, Madison, MS (US); Jeffrey Johnson, Flowood, MS (US); Morris Seymour, Huntsville, AL (US); Adam Lewis, Jackson, MS (US); Cyrus Ghavam, Huntsville, AL (US)

(73) Assignee: Spinal U.S.A., Pearl, MS (US)

( * ) Notice: Subject to any disclaimer, the term of this patent is extended or adjusted under 35 U.S.C. 154(b) by 538 days.

(21) Appl. No.: 12/567,978

(22) Filed: Sep. 28, 2009

Related U.S. Application Data

(60) Provisional application No. 61/101,737, filed on Oct. 1, 2008.

(51) Int. Cl.
*A61B 17/80* (2006.01)

(52) U.S. Cl.
USPC ............... 606/296; 606/295; 606/70; 606/71

(58) Field of Classification Search
USPC ................................. 606/280–299
See application file for complete search history.

(56) References Cited

U.S. PATENT DOCUMENTS

| | | | | |
|---|---|---|---|---|
| 5,951,558 | A * | 9/1999 | Fiz | 606/70 |
| 6,139,550 | A * | 10/2000 | Michelson | 606/70 |
| 6,306,139 | B1 * | 10/2001 | Fuentes | 606/70 |
| 7,288,094 | B2 * | 10/2007 | Lindemann et al. | 606/86 A |
| 7,306,605 | B2 * | 12/2007 | Ross | 606/70 |
| D592,946 | S * | 5/2009 | Johnson | D8/386 |
| 7,674,279 | B2 * | 3/2010 | Johnson | 606/295 |
| 7,727,266 | B2 * | 6/2010 | Lindemann et al. | 606/289 |
| 8,118,847 | B2 * | 2/2012 | Wallenstein et al. | 606/286 |
| 8,257,408 | B2 * | 9/2012 | Johnson et al. | 606/289 |
| 8,388,662 | B2 * | 3/2013 | LeHuec et al. | 606/280 |
| 8,454,667 | B2 * | 6/2013 | Humphreys | 606/289 |
| 2002/0147450 | A1 * | 10/2002 | LeHuec et al. | 606/61 |
| 2005/0027293 | A1 * | 2/2005 | LeHuec et al. | 606/61 |
| 2005/0059971 | A1 * | 3/2005 | Michelson | 606/69 |
| 2005/0075633 | A1 * | 4/2005 | Ross | 606/61 |
| 2005/0187552 | A1 * | 8/2005 | Michelson | 606/69 |
| 2005/0187553 | A1 * | 8/2005 | Grabowski et al. | 606/69 |
| 2005/0261690 | A1 * | 11/2005 | Binder et al. | 606/69 |
| 2006/0229620 | A1 * | 10/2006 | Rothman et al. | 606/69 |
| 2007/0043369 | A1 * | 2/2007 | Wallenstein et al. | 606/69 |
| 2008/0021470 | A1 * | 1/2008 | Ross | 606/61 |
| 2008/0091206 | A1 * | 4/2008 | Johnson | 606/69 |
| 2008/0255620 | A1 * | 10/2008 | Strauss et al. | 606/297 |
| 2009/0105830 | A1 * | 4/2009 | Jones et al. | 623/17.16 |
| 2009/0131988 | A1 * | 5/2009 | Bush et al. | 606/280 |
| 2009/0171397 | A1 * | 7/2009 | Rothman et al. | 606/280 |
| 2010/0234899 | A1 * | 9/2010 | Johnson et al. | 606/289 |
| 2011/0022097 | A1 * | 1/2011 | Walker et al. | 606/296 |
| 2012/0035665 | A1 * | 2/2012 | Suh | 606/295 |
| 2012/0158068 | A1 * | 6/2012 | Humphreys | 606/286 |
| 2012/0277803 | A1 * | 11/2012 | Remesh et al. | 606/289 |
| 2013/0204306 | A1 * | 8/2013 | Walker et al. | 606/289 |
| 2013/0218211 | A1 * | 8/2013 | Humphreys | 606/295 |

* cited by examiner

*Primary Examiner* — Michael T Schaper
(74) *Attorney, Agent, or Firm* — Cermak Nakajima LLP; Adam J. Cermak

(57) ABSTRACT

A bone plate, having a bone screw and a rotatable lock for retaining the bone screw in place, includes a retainer element and/or a stop element. The retainer element inhibits the lock from being pushed off of the bone plate, while the stop element limits the rotational range of motion of the lock.

6 Claims, 7 Drawing Sheets

BONE PLATE WITH RETAINER AND STOP FOR SCREW LOCK

This application claims priority under 35 U.S.C. §119 to U.S. provisional patent application No. 61/101,737, filed 1 Oct. 2008, the entirety of which is incorporated by reference herein.

BACKGROUND

1. Field of Endeavor

The present invention relates to devices, systems, and processes useful as bone plates, and more specifically to improvements in such plates fitted with screw locks.

2. Brief Description of the Related Art

U.S. Pat. No. D592,946 relates to a design of a rotatable lock for the bone screws used to hold bone plates to a bone, such as anterior cervical plates used in spinal surgeries. U.S. Patent Application Publication No. 2008/0091206, "Bone Plate", describes similar bone plates including rotatable screw locks. The entirety of each of these documents is incorporated by reference herein.

While the bone plates described in these patent documents perform well, in some circumstances the bone screws can back out of the bone to such an extent that the bone screw lock, which had been rotated over the head of the bone screw, is flexed upwards. Such flexing can cause damage to the bone screw lock, risking fracture of the lock. In addition, one difficulty that can arise with the use of such rotatable bone screw locks is that the practitioner does not have a way of knowing when the lock has been rotated the correct amount to adequately block the underlying bone screw from backing out, other than mere visual inspection.

There remains a need for improvements in bone screw locks which can address these and other issues.

SUMMARY

According to a first aspect of the invention, a bone plate comprises a plate formed of a biocompatible material and having an upper surface, at least one screw hole formed in the plate, and a stop element positioned on the plate upper surface, wherein, when a rotatable screw lock is rotatably mounted to the upper surface of the plate, at a position relative to the at least one screw hole so that, in a first unlocked position the screw lock does not impede passage of a bone screw through the at least one screw hole, and in a second locked position the screw lock does impede passage of a bone screw through the at least one screw hole, the stop element prevents the screw lock from complete rotation.

According to another aspect of the present invention, a bone plate comprises a plate formed of a biocompatible material and having an upper surface, at least one screw hole formed in the plate, and a retainer element positioned adjacent to the screw hole and forming a gap between the retainer and the plate upper surface, and wherein, when a rotatable screw lock is rotatably mounted to the upper surface of the plate, at a position relative to the at least one screw hole so that, in a first unlocked position the screw lock does not impede passage of a bone screw through the at least one screw hole, and in a second locked position the screw lock does impede passage of a bone screw through the at least one screw hole, the screw lock passes under the retainer element when moving between the first and second positions.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which.

DETAILED DESCRIPTION OF EXEMPLARY EMBODIMENTS

Figure 1:
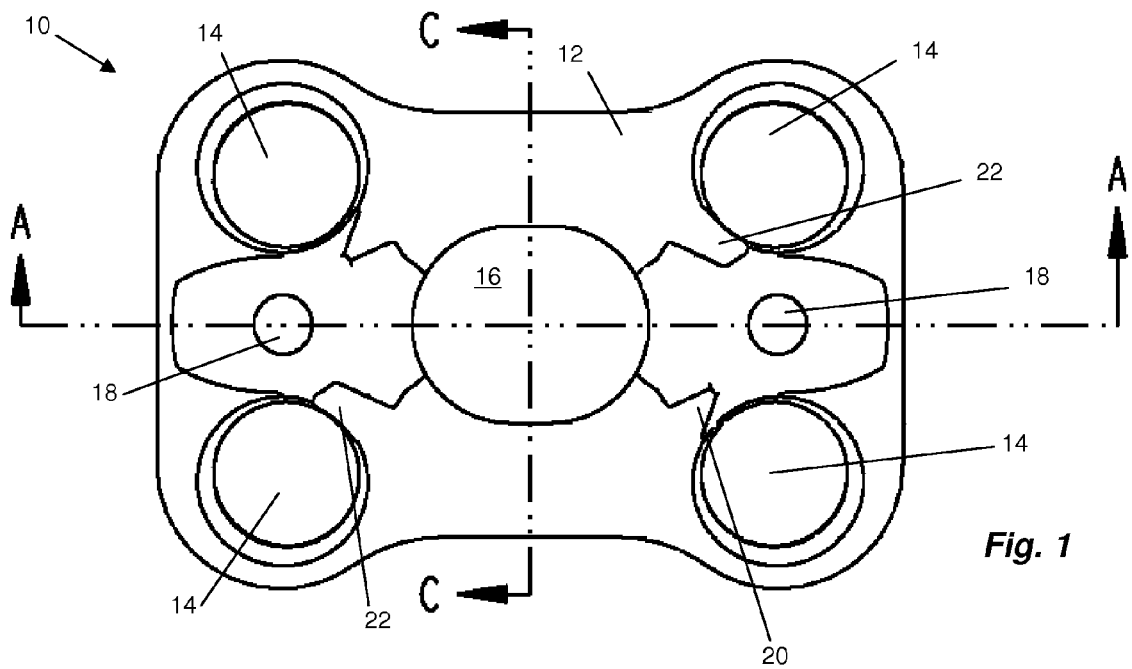
FIG. 1 illustrates a top plan view of a first exemplary embodiment of a bone plate in accordance with the present invention.

Referring to the drawing figures, like reference numerals designate identical or corresponding elements throughout the several figures.

The aforementioned two patent document describe bone plates and locks for the screws of bone plates; as those of ordinary skill in the art are well familiar with bone plates, screws for bone plates, and locks for the screws of bone plates, the details of those devices will not be included herein.

In general terms, in addition to the various features described in the two aforementioned patent documents, in accordance with principles of the present invention, a bone plate can be provided with a stop, a retainer, or both, for each one or more of the bone screw locks (also called a 'bow-tie rivet' herein). In essence, the stop is sized and positioned so that, when the bow-tie rivet is rotated in one direction, e.g., clockwise, the leading edge of the rivet hits the stop and prevents further rotational motion of the rivet. The lower surface of the retainer is spaced from the surface of the plate a distance sufficient to permit portions of the rivet to pass under the retainer as the rivet is rotated (e.g., clockwise); when the rivet's rotational motion ends, optionally because of the stop S, a portion of the rivet is still under the retainer R, which thus inhibits the rivet from popping off of the plate. Thus, by providing a stop to one side of the plate, when the practitioner turns the rivet, e.g., to 90 degrees, the rivet will hit against the stop and the practitioner thus knows to stop turning the rivet. Furthermore, the retainer can be provided so that when the rivet turns, it will stay under the retainer, so the rivet is inhibited or prevented from coming off of the plate.

The positions of the retainer and the stop, relative to the rotatable lock and to the screw holes, can be tailored to the particular application. Furthermore, the locations of the retainer and the stop can be swapped, that is, can be moved to accommodate clockwise or counterclockwise rotation of the lock. Furthermore, while the lock is illustrated as being positioned so that its top surface is above the upper surface of the bone plate, the lock can alternatively be recessed in the plate; in this configuration, the stop can be formed as a shoulder in the plate itself, rather than as an element extending above the plate's surface, and the retainer can be suitably lowered. Further optionally, the rotatable lock itself can be made asymmetrical, so that one lateral side of the lock is shorter than the other, so that the shorter side would not be impeded by the stop, yet still restrained by the retainer. Yet further alternatively, the stop and retainer can be either co-located, or incorporated into a single element that both overhangs the screw hole, including a space for a portion of the lock to reside, yet also includes a portion that blocks further rotational motion of the lock. All of the devices and components described herein are formed of biocompatible, implantable materials typically used for bone plates.

Turning now to the several drawing figures, exemplary bone plates embodying principles of the present invention are illustrated. In the top plan views of FIGS. 1 and 2, a bone plate 10 includes a generally flat body 12, which can include curvatures depending on the particular use for which the plate will be employed. The plate 10 includes at least one, and advantageously numerous screw holes 14 which pass entirely through the body 12 from the top to the bottom surfaces, and are sized and otherwise configured to receive a bone screw in each of the holes. Further optionally, the plate 10 can include one or more (one being illustrated) additional holes 16, for reducing the weight of the plate, among other purposes. One or more holes or bores 18 are formed in the body 12 to receive portions of a rotatable screw lock, described elsewhere herein and in the aforementioned U.S. patent documents; the holes 18 are positioned adjacent to at least one of the screw holes 14 so that when a screw lock is mounted in the hole 18, the screw lock can lock the head of a screw positioned in the hole 14.

As discussed above, the plate 10 includes a stop 20, a retainer 22, or both, in proximity to one or more of the holes 14. In the embodiment illustrated in FIG. 1, for each of the two pairs of bone screw holes on the left and right sides of the plate 10, a stop 20 is positioned immediately adjacent to one screw hole and a retainer 22 is positioned adjacent to the other screw hole of the pair. As a single bone screw lock is used to secure the bone screws in each pair of bone screw holes in this embodiment, the stop 20 and the retainer 22 are provided for each rotatable bone screw lock. According to other exemplary embodiments, more than one retainer, stop, or both, can be provided for each bone screw lock, regardless of the number of bone screws the particular lock secures to the plate 10.

Figure 3:
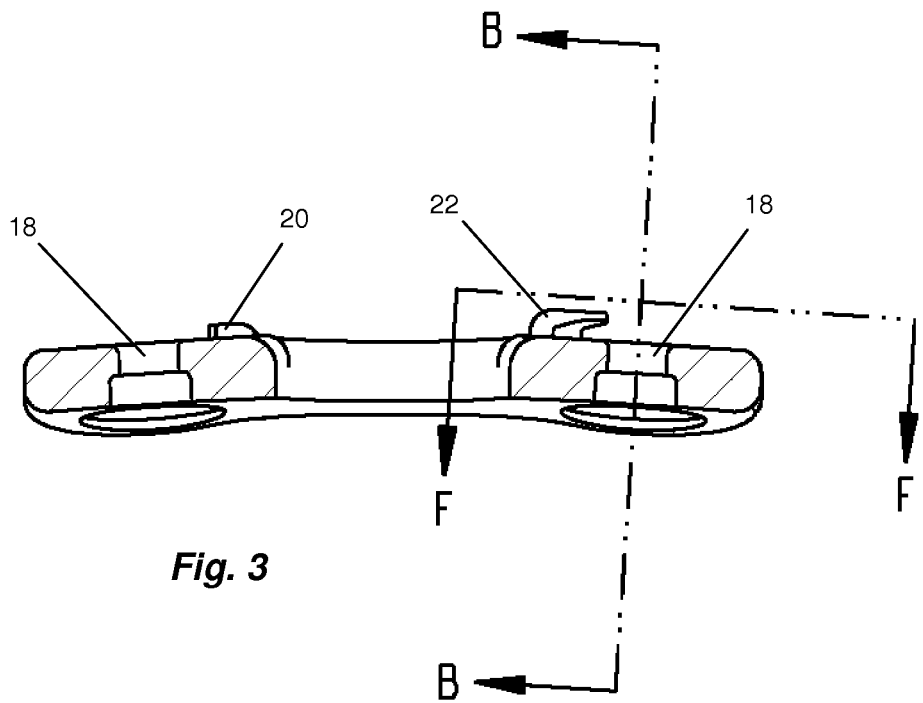
FIG. 3 illustrates a cross-sectional view of the device of FIG. 1, taken at line A-A.
Figure 4:
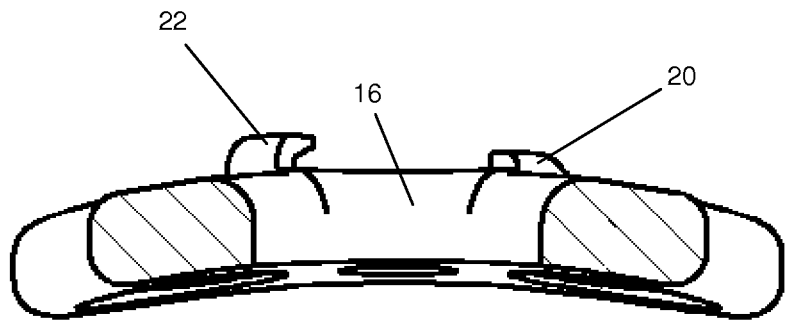
FIG. 4 illustrates a cross-sectional view of the device of FIG. 1, taken at line C-C.

FIGS. 3 and 4 illustrate a cross-sectional view, taken at lines A-A and C-C in FIG. 1, respectively, and show that the stop 20 need not extend far from the body 12 in order to prevent a rotatable bone screw lock from moving. Additionally, FIGS. 3 and 4 illustrate the overhanging feature of the retainer, which can inhibit or prevent a bone screw lock from popping off of the body 12.

Figure 2:
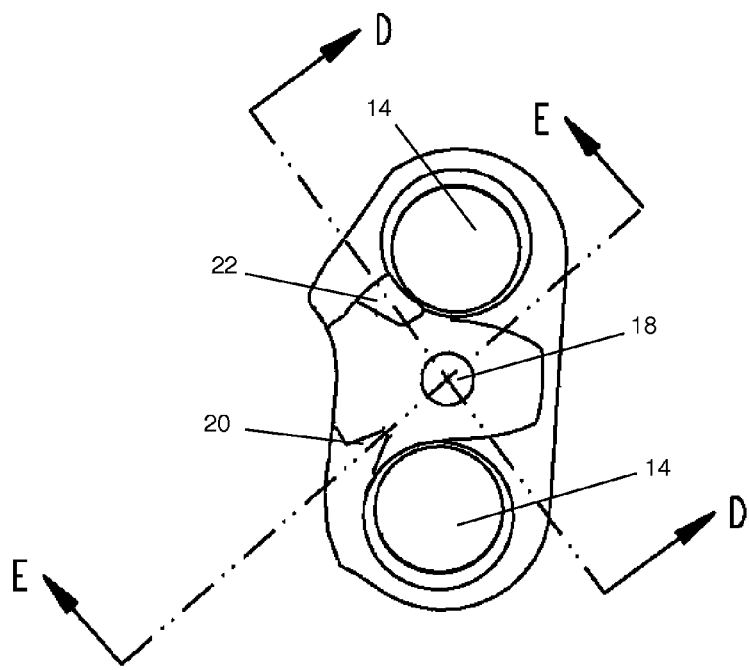
FIG. 2 illustrates an enlarged, top plan view of right side portions of the device illustrated in FIG. 1, taken at line F-F in FIG. 3.
Figure 5:
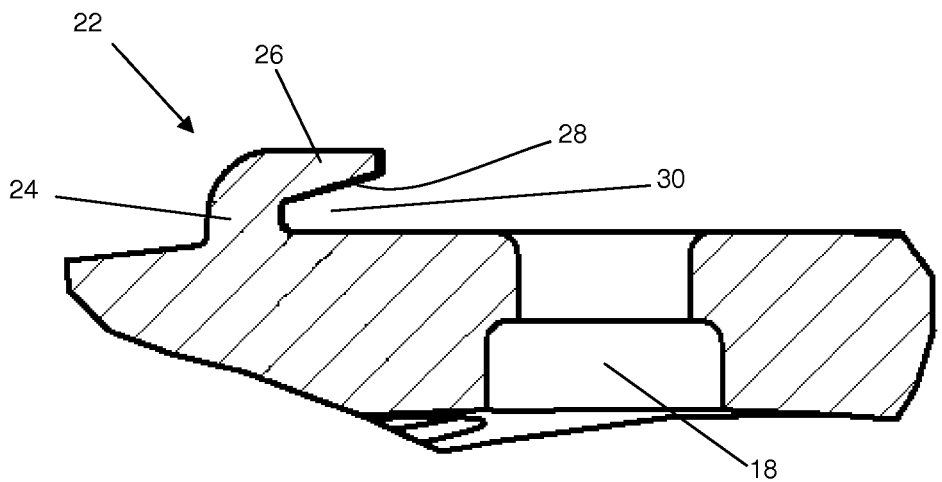
FIG. 5 illustrates a cross-sectional view of the device of FIG. 1, taken at line D-D in FIG. 2.

FIG. 5 illustrates a cross-sectional view, taken at line D-D of FIG. 2, of an exemplary retainer 22. The retainer 22 includes an upstanding portion 24 which is attached to the body 12 of the plate 10, and a laterally extending portion 26 which is attached to the upstanding portion 24. While the embodiment illustrated in FIG. 5 includes portions 24, 26 being integral with each other and with the body 12, other exemplary embodiments include these portions which are formed of one or more separate pieces which are joined together and joined to the body 12. The laterally extending portion has a bottom surface 28 which at least in part faces the top surface of the body 12 and defines a gap 30 between the bottom surface of the laterally extending portion and the top of the body 12. The gap 30 is sized and shaped to receive a portion of a bone screw lock therein and to thus inhibit or prevent the bone screw lock from moving vertically away from the body 12.

Figure 6:
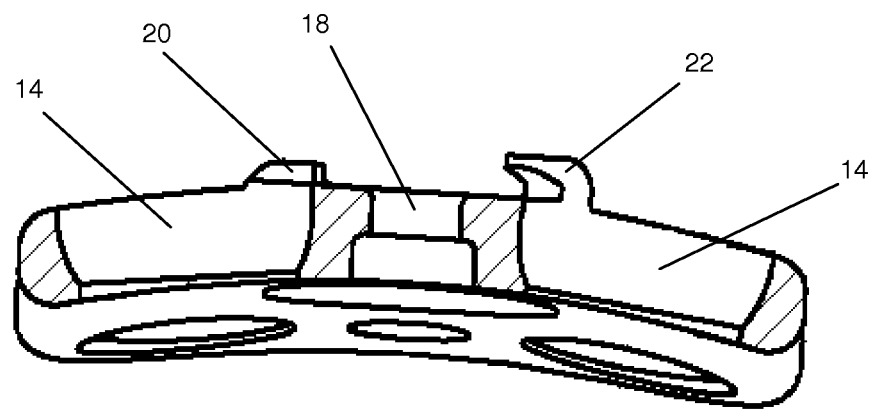
FIG. 6 illustrates a cross-sectional view of the device of FIG. 1, taken at line B-B in FIG. 3.
Figure 7:
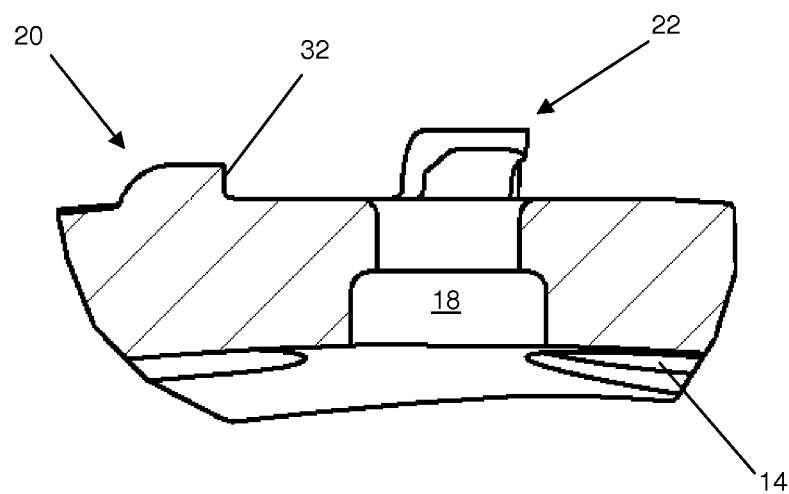
FIG. 7 illustrates a cross-sectional view of the device of FIG. 1, taken at line E-E in FIG. 2.

FIGS. 6 and 7 illustrate further cross-sectional views of the plate 10. As illustrated in FIG. 7, the stop 20 advantageously includes a vertically extending wall 32 which provides a well-defined position at which a bone screw lock will stop when rotated against the stop 20.

Figure 8:
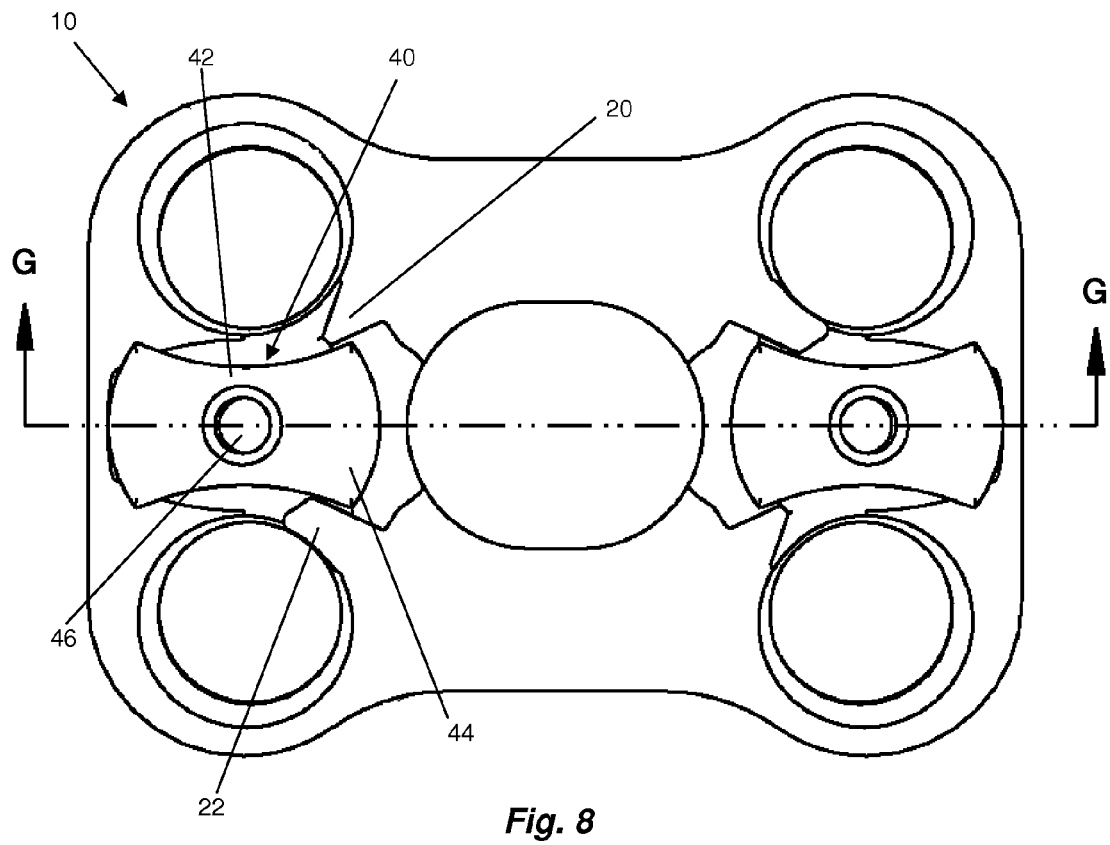
FIG. 8 illustrates a top plan view of the embodiment of FIG. 1, showing screw locks.

FIG. 8 illustrates a top plan view of the bone plate 10, with an exemplary rotatable bone screw lock 40 mounted to the body 12 at the hole 18. According to preferred embodiments, the lock 40 is configured and positioned on the body 12 in the manner described in the aforementioned two U.S. patent documents. The lock 40 includes a narrow central portion 42 and at least one, preferably two, and alternatively more than two, flared end portions 44 which extend outward from the central portion 42. As will be described in greater detail below, the configuration of the flared end portion(s) 44, the stop 20, and the retainer 22 are mutually dependent, and are constructed so that the lock 40 has at least two alternative rotary positions: a first position at which at least one of the adjacent bone screw holes 14 are unobstructed, so that a bone screw can be positioned in the bone screw hole; and a second position at which at least one of the flared end portions 42 overlies and obstructs the bone screw hole. In the second position, one of the flared end portions bears against the stop 20, and/or one of the flared end portions is at least partially under the laterally extending portion of a retainer 22 and in the gap 30. The lock 40 advantageously includes an opening 46 in the central portion 42 which can be configured to accept a torque driving tool (e.g., screwdriver, not illustrated) to assist the practitioner in rotating the lock 40 between its various rotary positions.

Figure 9:
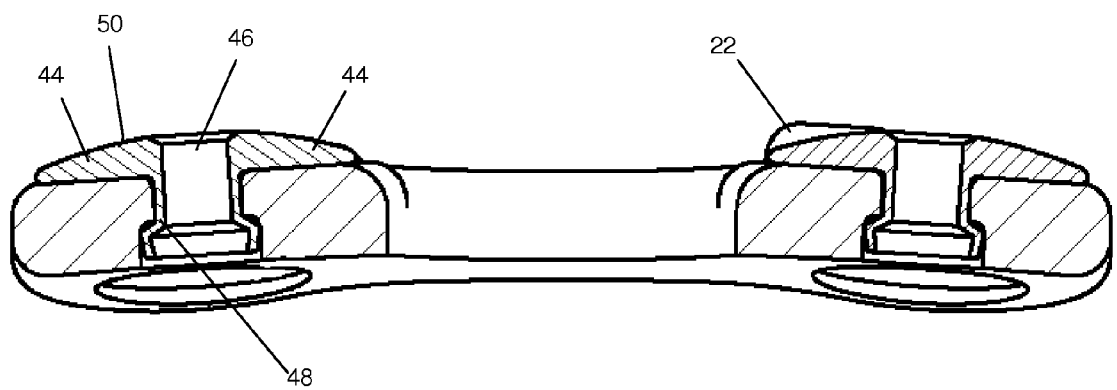
FIG. 9 illustrates a cross-sectional view of the device of FIG. 1, taken at line G-G in FIG. 8.

FIG. 9, which is a cross-sectional view taken at line G-G in FIG. 8, illustrates the top surface 50 the lock 40, a portion of which will be trapped beneath the laterally extending portion 30 when in the aforementioned second position. While the top surface 50 is illustrated as being convex and slightly dome-shaped, the top surface can be other shapes as well. The lock 40 optionally includes a vertically extending post 48, optionally formed of a deformable material, so that the lock can be rotatably secured to the plate body 12.

Figure 10:
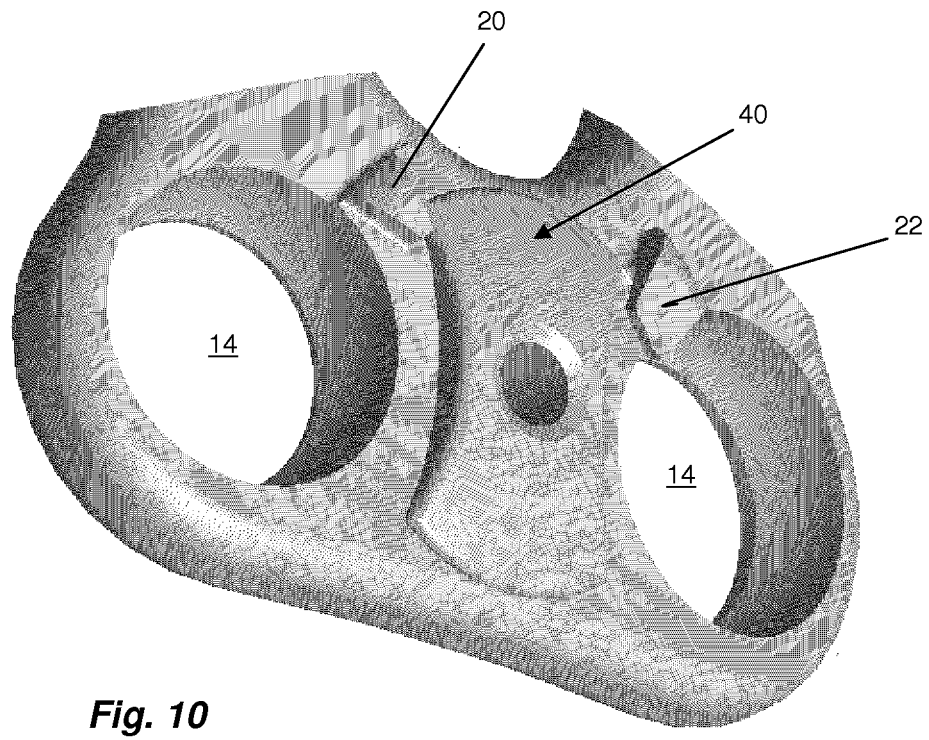
FIG. 10 illustrates a top, right, front perspective view of right side portions of FIG. 11, of the device of FIG. 8.
Figure 11:
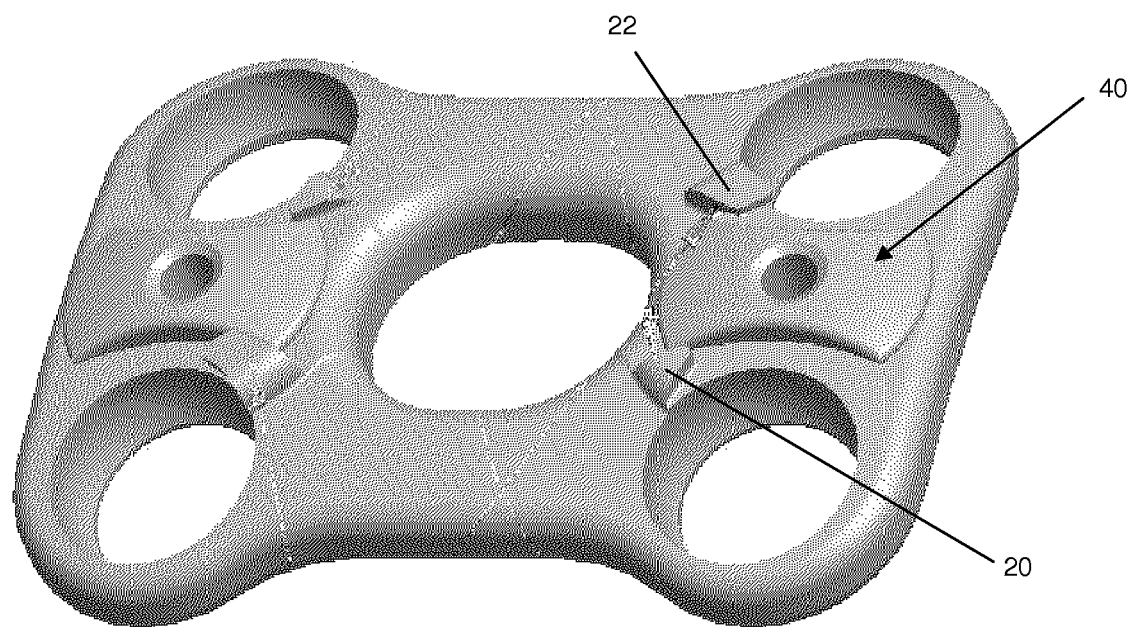
FIG. 11 illustrates a top, right, front perspective view of the device of FIG. 8.
Figure 12:
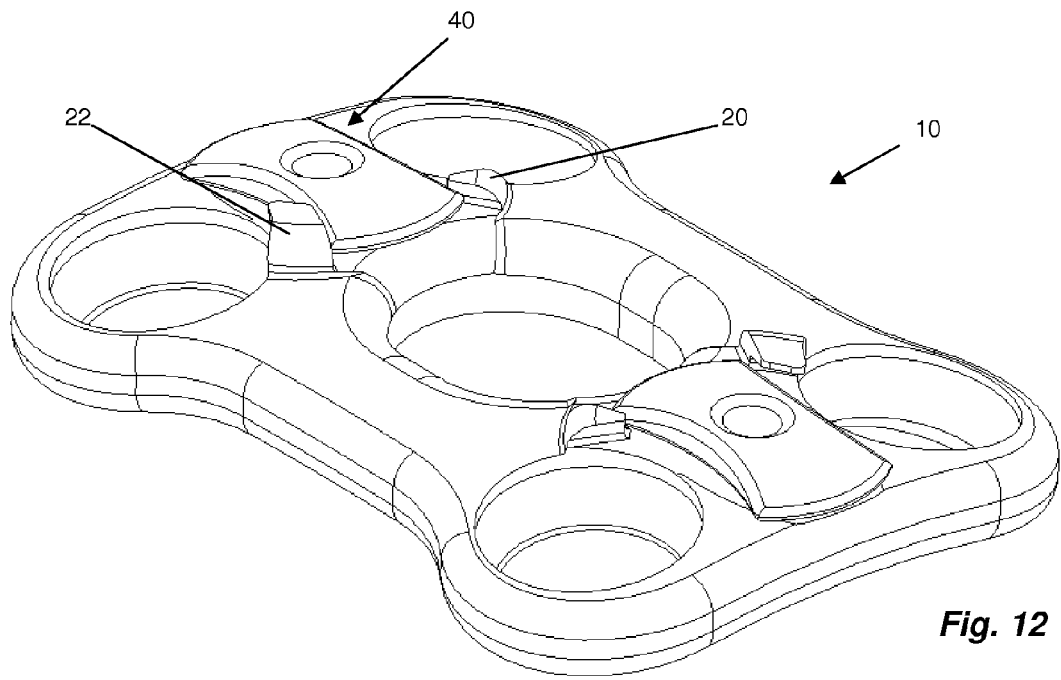
FIG. 12 illustrates another top, right, front perspective view of the device of FIG. 8, with the screw locks oriented in their 'unlocked' positions'.
Figure 13:
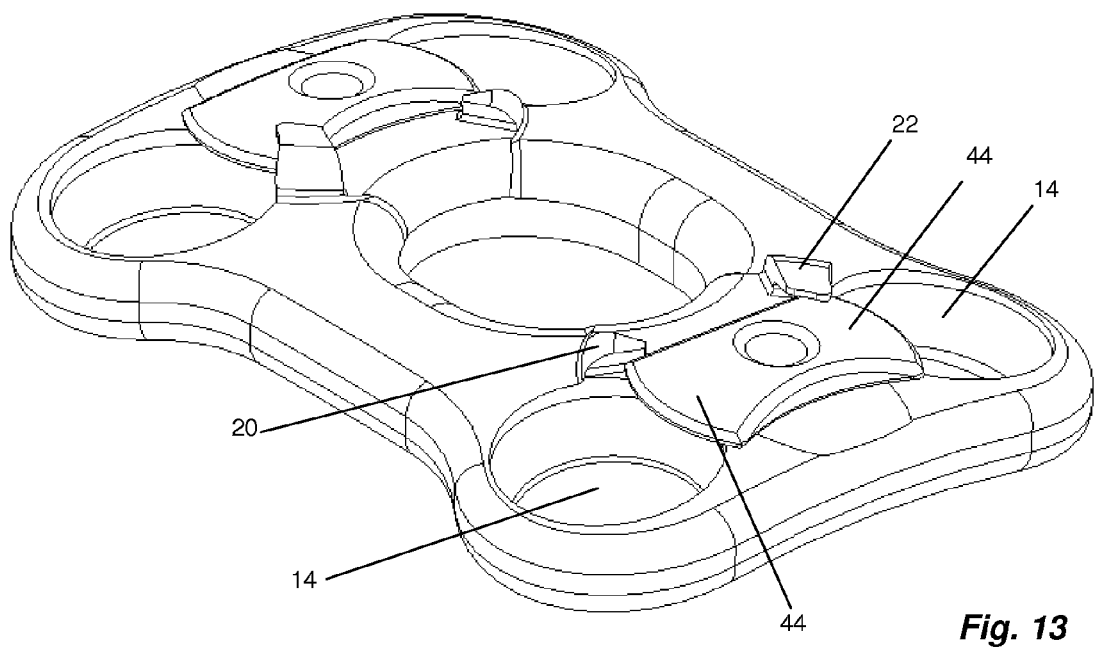
FIG. 13 illustrates the top, right, front perspective view of the device of FIG. 8, with the screw locks oriented in their 'locked' positions'.
Figure 14:
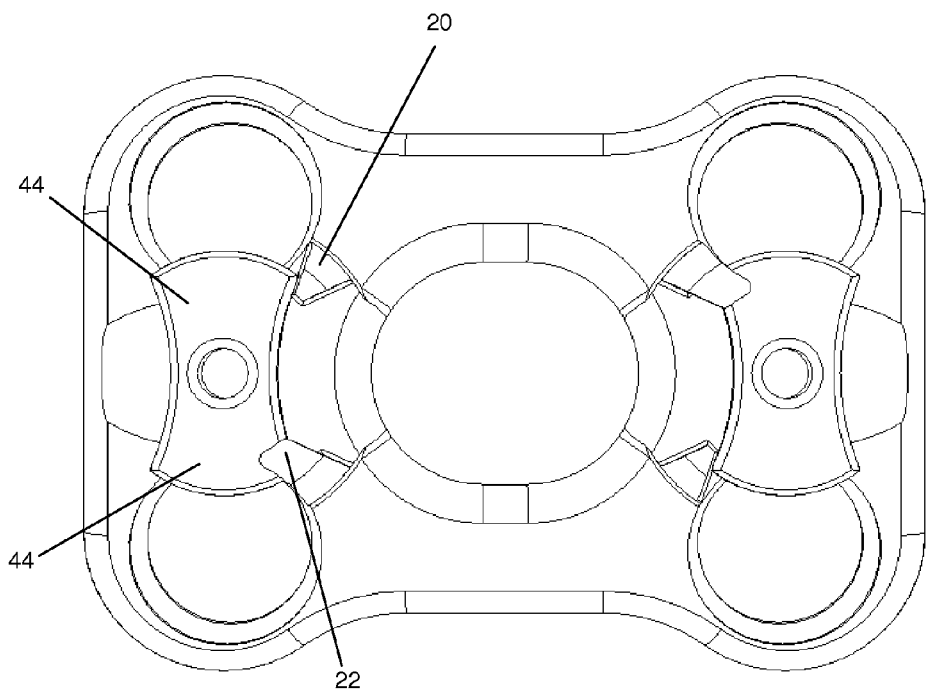
FIG. 14 illustrates a top plan view of the device of FIG. 8, with the screw locks oriented in their 'locked' positions.
Figure 15:
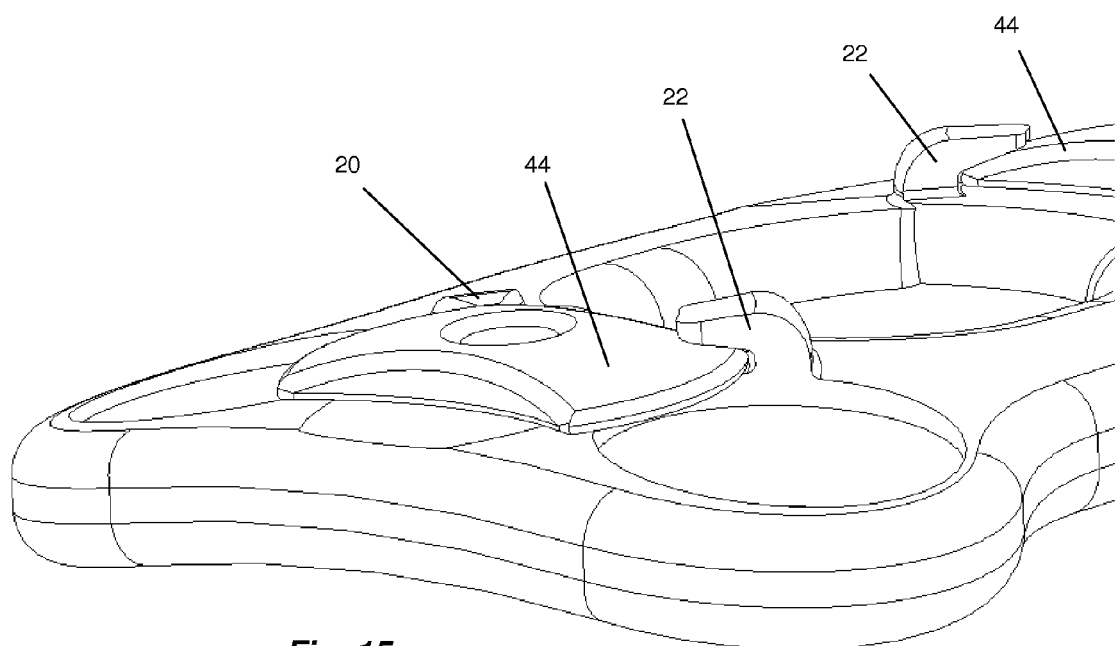
FIG. 15 illustrates a top, right, rear perspective view of right side portions of the device of FIG. 8, with the screw locks oriented in their 'locked' positions.

FIGS. 10-15 illustrate several perspective and plan views of the plate 10, with locks 40 in both the first (open) and second (locking) positions, and illustrate exemplary positions of the flanges 44 of the locks relative to the stop 20 and the retainer 22. FIGS. 10 and 11 illustrate perspective views of the plate 10 having both a stop 20 and a retainer 22, and a rotatable bone screw lock 40 rotated into an unlocked positioned, that is, the flanges 44 of the lock do not obstruct a bone screw hole 14. FIG. 12 illustrates a similar view, with two locks 40 in the same, unlocked orientation. FIG. 13 illustrates the same view as FIG. 12, but with the locks 40 rotated clockwise (as seen from above) into locking positions, that is, with the flanges 44 at least partially covering a hole 14. As can be seen in FIGS. 13-15, at least one of the flanges 44 is positioned under the laterally extending portion 26 of the retainer 22, and in the gap 30, when in the second position. Additionally, when provided with a stop 20, one of the flanges 44 abuts against the stop, and more particularly against the wall 32 in this embodiment. The stop 20 is thus advantageously positioned so that, when a flange 44 meets the stop, another portion of the lock 40, e.g., a flange of the lock, is under the laterally extending portion 26 and in the gap 30. The stop 20 can be eliminated from the plate 10, if desired.

According to further embodiments, the stop 20 and the retainer 22 can be located immediately adjacent to each other or integrated into a single structure, and the combination can be positioned as the retainers illustrated herein. Further optionally, the bottom surface 28 can be angled so that a flange 44 can enter into the gap 30, and upon further rotation of the lock 40 into the gap, the top surface 50 of the lock bears against the bottom surface 28 and locks the flange to the retainer 22. Yet further optionally, the bottom surface 28 and top surface 50 can be formed with cooperating snap-fit structures, such as one or more ridges and grooves, so that when the flange 44 is rotated into the gap 30 and the top surface 50 and bottom surface 28 bear against each other, the ridge(s) and groove(s) can snap together, thus forming a releasable lock.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

We claim:

1. A bone plate comprising:
a plate formed of a biocompatible material and having an upper surface;
a rotatable screw lock mounted to the plate upper surface, the screw lock including a central portion and a laterally extending flange, the screw lock being rotatable from a first, unlocked position to a second, locked position;
at least one screw hole formed in the plate;
a stop element positioned on the plate upper surface, the stop element including a side wall; and
a retainer element positioned adjacent to the screw hole and forming a gap between a portion of the retainer element and the plate upper surface; and
wherein, when the rotatable screw lock is in the first, unlocked position, the screw lock does not impede passage of a bone screw through the at least one screw hole, and, when in the second, locked position, the screw lock does impede passage of a bone screw through the at least one screw hole and the stop element prevents any portion of the screw lock from rotation beyond the stop element side wall, wherein a portion of the screw lock is positioned in the gap when in the second, locked position and no portion of the screw lock is positioned in the gap when in the first, unlocked position.

2. A bone plate according to claim 1, wherein the stop is positioned immediately adjacent to the retainer element.

3. A bone plate according to claim 1, wherein the retainer includes a laterally extending portion having a bottom surface, the bottom surface spaced from the plate upper surface, the gap being located between the laterally extending portion bottom surface and the plate upper surface.

4. A bone plate according to claim 1, wherein the stop element side wall includes a vertically extending wall.

5. A bone plate according to claim 1, wherein the stop element is positioned remotely from a first screw hole of the at least one screw hole.

6. A bone plate comprising:
a plate formed of a biocompatible material and having an upper surface;
a screw lock hole extending through the plate, the screw lock hole including a shoulder;
a rotatable screw lock mounted in the screw lock hole, the screw lock including a central portion with a post extending away from the plate upper surface, and a laterally extending flange, the screw lock being rotatable from a first, unlocked position to a second, locked position, and the screw lock post including a flared portion bearing against said screw lock hole shoulder and rotatably securing said screw lock to said plate;
at least one screw hole formed in the plate adjacent to said screw lock hole; and
a stop element positioned on the plate upper surface, the stop element including a side wall; and
a retainer element positioned adjacent to the screw hole and forming a gap between a portion of the retainer element and the plate upper surface;
wherein, when the rotatable screw lock is in the first, unlocked position, the screw lock does not impede passage of a bone screw through the at least one screw hole, and, when the rotatable screw lock is in the second, locked position, the screw lock does impede passage of a bone screw through the at least one screw hole and the stop element prevents any rotation of the screw lock from rotation beyond the stop element side wall, a portion of the screw lock positioned in the gap when in the second position.

* * * * *

UNITED STATES PATENT AND TRADEMARK OFFICE
CERTIFICATE OF CORRECTION

| | | |
|---|---|---|
| PATENT NO. | : 8,652,182 B1 | Page 1 of 1 |
| APPLICATION NO. | : 12/567978 | |
| DATED | : February 18, 2014 | |
| INVENTOR(S) | : Walker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 554 days.

Signed and Sealed this
Twenty-first Day of July, 2015

Michelle K. Lee
*Director of the United States Patent and Trademark Office*